(12) United States Patent
Cha et al.

(10) Patent No.: US 11,643,638 B2
(45) Date of Patent: May 9, 2023

(54) METHOD FOR PRODUCING STEM CELL-DERIVED EXTRACELLULAR VESICLE

(71) Applicants: SAMSUNG ELECTRONICS CO., LTD., Suwon-si (KR); S & E BIO CORPORATION, Seoul (KR)

(72) Inventors: Jae Min Cha, Seoul (KR); Oh Young Bang, Seoul (KR); Gyeong Joon Moon, Seongnam-si (KR); Eun Kyoung Shin, Seoul (KR)

(73) Assignees: Samsung Electronics Co., Ltd., Suwon-si (KR); S & E Bio Corporation, Seoul (KR)

( * ) Notice: Subject to any disclaimer, the term of this patent is extended or adjusted under 35 U.S.C. 154(b) by 606 days.

(21) Appl. No.: 16/097,452

(22) PCT Filed: Apr. 29, 2016

(86) PCT No.: PCT/KR2016/004542
§ 371 (c)(1),
(2) Date: Oct. 29, 2018

(87) PCT Pub. No.: WO2017/188487
PCT Pub. Date: Nov. 2, 2017

(65) Prior Publication Data
US 2019/0144830 A1 May 16, 2019

(51) Int. Cl.
*C12N 5/0775* (2010.01)
*A61K 35/28* (2015.01)

(52) U.S. Cl.
CPC ............ *C12N 5/0662* (2013.01); *A61K 35/28* (2013.01); *C12N 5/0663* (2013.01); *C12N 2510/02* (2013.01); *C12N 2513/00* (2013.01)

(58) Field of Classification Search
CPC ............... C12N 5/0662; C12N 5/0663; C12N 2510/02; C12N 2513/00; A61K 35/28
See application file for complete search history.

(56) References Cited

FOREIGN PATENT DOCUMENTS

KR 10-2013-0116552 10/2013
WO 2015/016761 2/2015

OTHER PUBLICATIONS

2) Moeller HC, Mian MK, Shrivastava S, Chung BG, Khademhosseini A. A microwell array system for stem cell culture. Biomaterials. Feb. 2008;29(6):752-63. doi: 10.1016/j.biomaterials.2007.10.030. Epub Nov. 14, 2007. PMID: 18001830; Pmcid: PMC2253687 (Year: 2007).*
1) Jarmalavičiūtė A, Tunaitis V, Pivoraitė U, Venalis A, Pivoriūnas A. Exosomes from dental pulp stem cells rescue human dopaminergic neurons from 6-hydroxy-dopamine-induced apoptosis. Cytotherapy. Jul. 2015;17(7):932-9. doi: 10.1016/j.jcyt.2014.07.013. Epub May 13, 2015. PMID: 25981557. (Year: 2015).*
Lei Y, Schaffer DV. A fully defined and scalable 3D culture system for human pluripotent stem cell expansion and differentiation. Proc Natl Acad Sci U S A. Dec. 24, 2013;110(52):E5039-48. doi: 10.1073/pnas.1309408110. Epub Nov. 18, 2013. PMID: 24248365; PMCID: PMC3876251. (Year: 2013).*
Zare S, Kurd S, Rostamzadeh A, Nilforoushzadeh M A. Types of Stem Cells in Regenerative Medicine: A Review, J Skin Stem Cell. 2014; 1(3):e28471. doi: 10.17795/jssc28471. (Year: 2014).*
Baraniak PR, McDevitt TC. Scaffold-free culture of mesenchymal stem cell spheroids in suspension preserves multilineage potential. Cell Tissue Res. 2012;347(3):701-711 (Year: 2012).*
Katsuda T, Tsuchiya R, Kosaka N, Yoshioka Y, Takagaki K, Oki K, Takeshita F, Sakai Y, Kuroda M, Ochiya T. Human adipose tissue-derived mesenchymal stem cells secrete functional neprilysin-bound exosomes. Sci Rep. 2013;3:1197. (Year: 2013).*
Qiu X, Zhang Y, Zhao X, Zhang S, Wu J, Guo H, Hu Y. Enhancement of endothelial differentiation of adipose derived mesenchymal stem cells bya three-dimensional culture system of microwell. Biomaterials. 2015;53:600-8. (Year: 2015).*
Yu B, Zhang X, Li X. Exosomes derived from mesenchymal stem cells. Int J Mol Sci. 2014;15(3):4142-4157. Published Mar. 7, 2014 (Year: 2014).*
Sart (Tissue Engineering, 2014, 20:365-380).*
Yeo (Advanced Drug Delivery Reviews 65 (2013) 336-34).*
Timmers (2011, Stem Cell Research, 6:206-214).*
Exocarta, printout attached, http://exocarta.org/gene_summary?gene_id=3589 accessed on Mar. 10, 2022, 2 pages.*
Katsuda, Expert Opinion on Biological Therapy, 15:4, 495-504.*
Xie, Frontiers in Immunology, 2020, 11:1-16.*
Del Fattore, Expert Opinion on Biological Therapy, 15:4, 495-504.*
International Search Report for PCT/KR2016/004542 dated Jan. 24, 2017, 5 pages.
Written Opinion of the ISA for PCT/KR2016/004542 dated Jan. 24, 2017, 7 pages.
Jarmalaviciute et al., "Exosomes from Dental Pulp Stem Cells Rescue Human Dopaminergic Neurons from 6-hydroxy-dopamine-induced Apoptosis", Cytotherapy, vol. 7, issue 17, pp. 932-939 (2015).
Lao et al., "Improved Methods to Generate Spheroid Cultures from Tumor Cells, Tumor Cells and Fibroblasts or Tumor-fragments: Microenvironment, Microvesicles and MiRNA", Plos One, vol. 10, issue 7, article No. e0133895 (internal pp. 1-19) (2015).
Cordey et al., "Enhancing the Reliability and Throughput of Neurosphere Culture on Hydrogel Microwell Arrays", Stem Cells, vol. 26, No. 10, pp. 2586-2594 (2008) (39 pages).
Uluc et al., "Focal Cerebral Ischemia Model by Endovascular Suture Occlusion of the Middle Cerebral Artery in the Rat", Journal of Visualized Experiments, 5 pages (2011).
(Continued)

Primary Examiner — Valarie E Bertoglio
(74) Attorney, Agent, or Firm — Nixon & Vanderhye P.C.

(57) ABSTRACT

Provided are a method for producing stem cell-derived extracellular vesicles by using a three-dimensional cell culture process, use of three-dimensional cell aggregates of stem cells in producing extracellular vesicles, a culture of three-dimensional cell aggregates of stem cells comprising a high concentration of extracellular vesicles, and a pharmaceutical composition comprising the culture.

8 Claims, 13 Drawing Sheets

(56) References Cited

OTHER PUBLICATIONS

György et al., "Membrane vesicles, current state-of-the-art: emerging role of extracellular vesicles", Cellular and Molecular Life Sciences, vol. 68, pp. 2667-2688 (2011).

* cited by examiner

FIG. 2
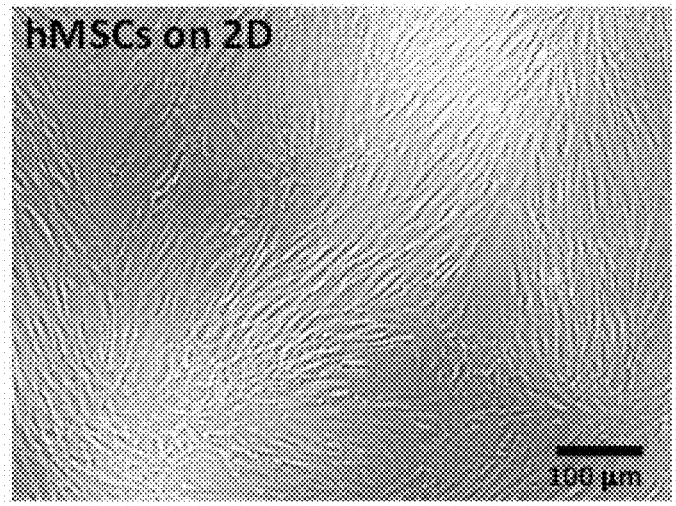
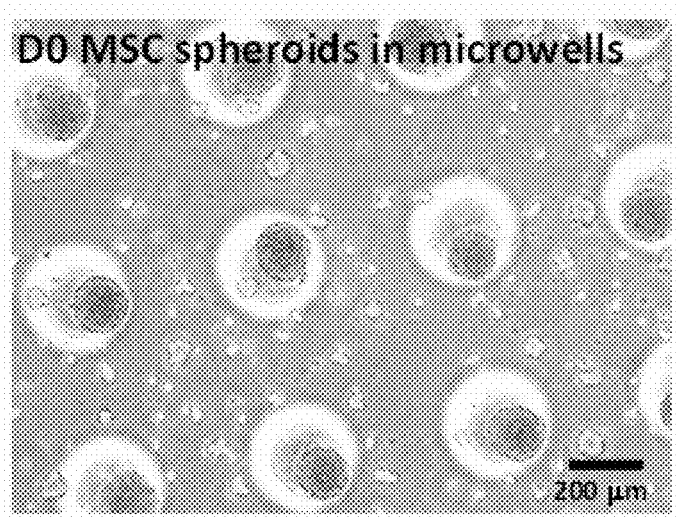

FIG. 10
hMSC-aggregates
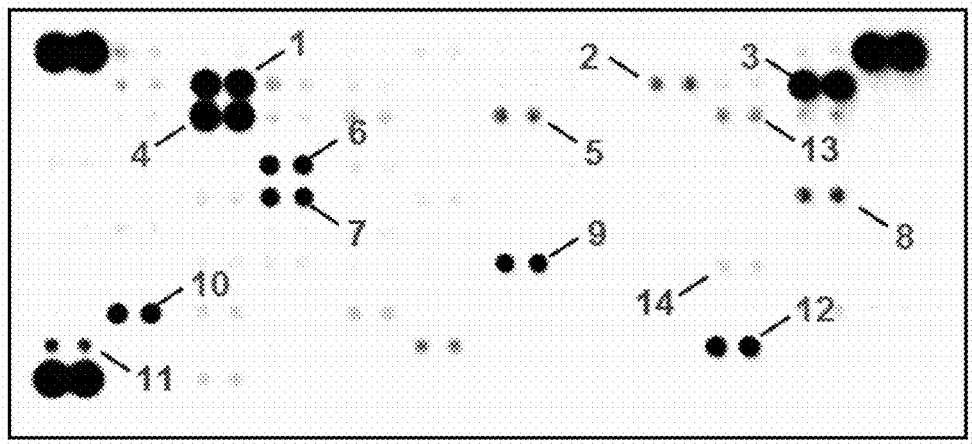
hMSCs treated with IBE
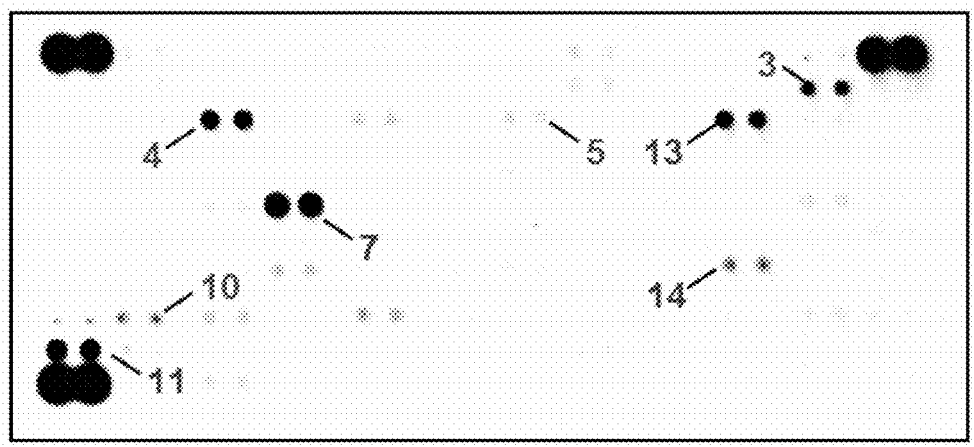

METHOD FOR PRODUCING STEM CELL-DERIVED EXTRACELLULAR VESICLE

This application is the U.S. national phase of International Application No. PCT/KR2016/004542 filed Apr. 29, 2016 which designated the U. S, the entire contents of which are hereby incorporated by reference.

TECHNICAL FIELD

The present disclosure relates to a method of producing stem cell-derived extracellular vesicles using a three-dimensional cell culture process, use of three-dimensional cell aggregates of stem cells in producing extracellular vesicles, a culture of three-dimensional cell aggregates of stem cells including a high concentration of extracellular vesicles, and a pharmaceutical composition including the culture.

BACKGROUND ART

As a new paradigm for treating incurable/intractable diseases, adult stem cell therapy has been widely applied in clinical trials and many successful cases have been reported.

However, there are problems of zoonosis caused by internalization of xenogenic serum (e.g., fetal bovine/calf serum) during ex vivo culture to proliferate stem cells which are extracted/selected from patients or donors, a problem of tumor formation caused by stem cell characteristics such as a vigorous proliferation capacity, a relatively large cell size, etc., when stem cells are transplanted into the body, risk factors such as vascular occlusion causing infarcts, etc., and therefore, it is necessary to find solutions for successful stem cell injection/transplantation therapy.

In addition, there is a limit to the versatility of stem cell therapy, because therapeutic efficacies of stem cells in terms of extracellular proliferation ability of stem cells, migration ability to a lesion, therapeutic factor secretion ability, etc., differ between patients when a therapy using autologous stem cells is applied.

Therefore, many studies have been actively conducted to avoid the various risk factors or problems that may arise from the direct use of living stem cells mentioned above. Some of the studies have reported results that stem cell-derived extracellular vesicles may replace therapeutic functions of stem cells (Cell. Mol. Life Sci. (2011) 68: 2667-2688).

Therapies using stem cell-derived extracellular vesicles have emerged, which may replace direct injection/transplantation of living stem cells. The therapy has shown many efficacies in pre-clinical trials, and some cases have been reported to have entered clinical trials.

Existing stem cell cultures are performed by extracting and selecting stem cells from a patient or a donor and proliferating them in a two-dimensional culture plate. It is known that when adult stem cells are cultured in a two-dimensional culture plate in a laboratory, biological properties such as the original stem cell ability and therapeutic factor secretion ability are remarkably reduced.

Several preclinical studies of stem cell-derived extracellular vesicles have demonstrated their therapeutic efficacy, but stem cells cultured in a laboratory by the existing two-dimensional culture technique have a very low secretion ability of extracellular vesicles. Thus, there is a problem in that the yield of extracellular vesicles is too low for use as therapeutic agents. Recently, it has been reported that extracellular vesicle secretion of stem cells is rather successfully enhanced by culturing mesenchymal stem cells under hypoxic conditions. However, the yield is still low, and is insufficient to be applied in clinical treatments.

To extend the range of application of therapeutic stem cell-derived extracellular vesicles from the research stage to practical clinical treatments, there is a need to develop techniques of mass-producing extracellular vesicles in quantities sufficient to be administered to patients.

DESCRIPTION OF EMBODIMENTS

Technical Problem

To solve such a problem of low yield, provided is a method of mass-producing stem cell-derived extracellular vesicles in a clinically applicable scale, wherein three-dimensional culture of stem cells is performed to form conditions similar to an in vivo environment, thereby increasing the activity and functionality of stem cells.

An aspect provides a method of producing stem cell-derived extracellular vesicles, the method including performing three-dimensional culture of stem cells.

Another aspect provides a composition for producing stem cell-derived extracellular vesicles, the composition including stem cell aggregates formed by three-dimensional culture of stem cells.

Still another aspect provides use of the stem cell aggregates formed by three-dimensional culture of stem cells in producing the stem cell-derived extracellular vesicles.

Still another aspect provides a culture obtained by culturing the stem cell aggregates.

Still another aspect provides a pharmaceutical composition including the culture obtained by culturing the stem cell aggregates.

Solution to Problem

It was demonstrated that three-dimensional culture of stem cells allows cells to spontaneously aggregate to form cell aggregates, and creates environments and/or conditions similar to in vivo cell proliferation environments and/or conditions of three-dimensional tissues from which the stem cells are originated, and as a result, original biological activities of stem cells including stemness, therapeutic factor secretion ability, etc., may be recovered or enhanced even during experimental culture. For example, when mesenchymal stem cells (MSCs) are cultured by three-dimensional culture, self-aggregation of cells occurs, which is similar to mesenchymal condensation events generated in mesenchymal tissues in vivo, and as a result, original biological activities of stem cells may be recovered or enhanced.

Thus, it is suggested that when cell aggregates are formed through three-dimensional culture of stem cells, in vivo-like microenvironment is created, and original activities of stem cells are recovered or enhanced, and accordingly, it is possible to mass-produce extracellular vesicles secreted from stem cells.

An aspect of the present disclosure provides a method of producing stem cell-derived extracellular vesicles, the method including performing three-dimensional culture of stem cells.

As used herein, the stem cells may be used to encompass embryonic stem cells, adult stem cells, induced pluripotent stem cell (iPS cells), and progenitor cells. For example, the stem cells may be one or more selected from the group consisting of embryonic stem cells, adult stem cells, induced pluripotent stem cells, and progenitor cells. The stem cells may be homologous stem cells and/or autologous stem cells.

The embryonic stem cells may be stem cells derived from embryos, in which stem cells have the ability to differentiate into cells of any tissue.

The induced pluripotent stem cells (iPS cells) are also called dedifferentiated stem cells and refer to cells having pluripotency, like embryonic stem cells, which is induced by injecting a cell differentiation-related gene into a differentiated somatic cell and returning it to a cell stage before differentiation.

The progenitor cells have ability to differentiate into a specific type of cells, similar to stem cells, but the progenitor cells are more specific and targeted than stem cells, and undergo a finite number of divisions, unlike stem cells. The progenitor cells may be mesenchymal progenitor cells, but are not limited thereto. In the present disclosure, the progenitor cells are included in category of the stem cells, and unless otherwise mentioned, the 'stem cells' are interpreted as including the progenitor cells.

The adult stem cells are stem cells extracted from the cord blood (umbilical cord blood) or adult bone marrow, blood, nerve, etc., and refer to primitive cells immediately before they are differentiated into cells of specific organs. The adult stem cells may be one or more selected from the group consisting of hematopoietic stem cells, mesenchymal stem cells, and neural stem cells. The adult stem cells may be adult stem cells of mammals, e.g., humans. The adult stem cells are advantageously applied to the treatment of incurable/intractable diseases, because various kinds of adult stem cells are used to regenerate various organs practically needed in medicine and the adult stem cells may differentiate according to properties of the organs after transplantation, whereas they are difficult to proliferate and tend to easily differentiate.

In one embodiment, the adult stem cells may be mesenchymal stem cells, for example, human mesenchymal stem cells. The mesenchymal stem cells (MSCs) are, also called mesenchymal stromal cells (MSC), multipotent stromal cells that may differentiate into various kinds of cells such as osteoblasts, chondrocytes, myocytes, adipocytes, etc. The mesenchymal stem cells may be selected from multipotent cells derived from non-marrow tissues such as placenta, umbilical cord blood, adipose tissues, adult muscle, corneal stroma, dental pulp of baby teeth, etc.

The extracellular vesicle means a particle-shaped structure, in which various biomolecules, such as proteins having various functions (e.g., various growth factors, chemokines, cytokines, transcription factors, etc.), RNAs (mRNA, miRNA, etc.), lipids which are released (secreted) from cells into the extracellular environment, are enclosed by lipid bilayer membranes the same as membranes of cells from which the biomolecules are derived.

The extracellular vesicle may be a stem cell-derived extracellular vesicle.

The stem cell-derived extracellular vesicle may be any vesicle having an average diameter of about 50 nm to about 1 micrometer (μm) which is released by a stem cell, and specifically, a vesicle (also called microvesicle) having an average diameter of about 100 nm to about 1 μm or a vesicle (also called exosome) having an average diameter of about 50 nm to about 100 nm, which is released by a stem cell, or a mixture thereof. In the present disclosure, extracellular vesicle, microvesicle, and exosome may be used interchangeably with each other regardless of size, unless otherwise mentioned.

The stem cell-derived extracellular vesicle is a particle structure enclosed by a cell membrane of a stem cell from which the vesicle is derived. The stem cell-derived extracellular vesicle may include not only useful biomolecules such as proteins, nucleotides, etc., but also, as vesicle membranes, all cell membrane components including various receptors and channels located in the cell membranes of the stem cell from which the vesicle is derived, and therefore, the stem cell-derived extracellular vesicle may play an important role in cell-to-cell communication and interaction with the surrounding micro-environment which are performed by the stem cells through the cell membrane components.

Further, since various receptors located in the membrane of the extracellular vesicle may specifically bind to a specific ligand present in the cell membrane or extracellular matrix of other cells, it is possible to target a specific cell, tissue, or micro-environment.

Further, in the extracellular vesicle, various biomolecules, such as proteins having various functions, RNAs, lipids, are enclosed by lipid bilayer membranes, which may protect the inner enclosure from degradation enzymes and/or degradation chemicals to extend the shelf life thereof.

Therefore, as compared with direct extracellular release of therapeutically useful biomolecules from stem cells, release of the biomolecules enclosed in the extracellular vesicle may allow safer and more selective target delivery, and may also be involved in cell-to-cell communication. Thus, it is advantageous in that the biomolecules may exert their functions more appropriately and effectively. Due to this advantage, importance of the stem cell-derived extracellular vesicle has been increasing in various therapies using stem cells.

When stem cells are cultured on a plate by two-dimensional culture as in the existing culture methods, they are cultured in a two-dimensional planar structure of a monolayer. However, an in vivo tissue, from which stem cells are derived, has a three-dimensional structure, not a two-dimensional planar structure. A cell culture of a monolayer which is produced by the existing two-dimensional cell culture process shows a reduction in cell-to-cell contact, as compared with a three-dimensional tissue. Thus, interactions between cells or between a cell and an extracellular matrix (ECM), as in a three-dimensional tissue in vivo, may not occur. As described above, when stem cells are cultured by the existing culture methods, a yield of the extracellular vesicle is very low, which becomes an obstacle in using the extracellular vesicle as a therapeutic agent. It is considered that the low yield is associated with destruction of interactions between cells or between a cell and an extracellular matrix (ECM) which are related to the secretion of extracellular vesicles by stem cells in vivo during two-dimensional cell culture.

In the present disclosure, as suggested above, when stem cells are cultured by the three-dimensional cell culture method, three-dimensional cell aggregates are produced by self-aggregation of cells. The three-dimensional cell aggregates thus produced may provide an environment similar to that of in vivo tissue from which the stem cells are derived. As a result, their functions in the communication between the stem cells become similar to those in vivo, and extracellular vesicles may be produced under the environment relatively similar to that of in vivo, leading to improvement of the production yield of extracellular vesicles.

Accordingly, the method of producing the stem cell-derived extracellular vesicles may include producing three-dimensional cell aggregates by culturing stem cells by three-dimensional cell culture.

The three-dimensional cell aggregate produced by three-dimensional cell culture may have, for example, a spheroidal structure, but is not limited thereto. The cell aggregate may have an average diameter of about 50 micrometer (μm) or more, about 70 μm or more, about 100 μm or more, about 130 μm or more, about 150 μm or more, or about 170 μm or more to realize the three-dimensional structure similar to in vivo tissue, and the cell aggregate may have an average diameter of about 250 μm, about 230 μm or less, or about 200 μm or less to prevent necrosis of the cells inside the aggregate due to oxygen depletion. For example, the cell aggregate may be a three-dimensional cell aggregate having an average diameter of about 50 μm to about 250 μm, about 50 μm to 230 μm, about 50 μm to about 200 μm, about 70 μm to about 250 μm, about 70 μm to 230 μm, about 70 μm to about 200 μm, about 100 μm to about 250 μm, about 100 μm to 230 μm, about 100 μm to about 200 μm, about 130 μm to about 250 μm, about 130 μm to 230 μm, about 130 μm to about 200 μm, about 150 μm to about 250 μm, about 150 μm to 230 μm, about 150 μm to about 200 μm, about 170 μm to about 250 μm, about 170 μm to 230 μm, or about 170 μm to about 200 μm.

The number of the stem cells included in the three-dimensional cell aggregate may be about 10 cells to about 2500 cells, about 15 cells to about 2500 cells, about 20 cells to about 2500 cells, about 100 cells to about 2500 cells, about 200 cells to about 2500 cells, about 300 cells to about 2500 cells, about 400 cells to about 2500 cells, about 10 cells to about 2000 cells, about 15 cells to about 2000 cells, about 20 cells to about 2000 cells, about 100 cells to about 2000 cells, about 200 cells to about 2000 cells, about 300 cells to about 2000 cells, about 400 cells to about 2000 cells, about 10 cells to about 1500 cells, about 15 cells to about 1500 cells, about 20 cells to about 1500 cells, about 100 cells to about 1500 cells, about 200 cells to about 1500 cells, about 300 cells to about 1500 cells, about 400 cells to about 1500 cells, about 10 cells to about 1250 cells, about 15 cells to about 1250 cells, about 20 cells to about 1250 cells, about 100 cells to about 1250 cells, about 200 cells to about 1250 cells, about 300 cells to about 1250 cells, about 400 cells to about 1250 cells, about 10 cells to about 1000 cells, about 15 cells to about 1000 cells, about 20 cells to about 1000 cells, about 100 cells to about 1000 cells, about 200 cells to about 1000 cells, about 300 cells to about 1000 cells, about 400 cells to about 1000 cells, about 10 cells to about 800 cells, about 15 cells to about 800 cells, about 20 cells to about 800 cells, about 100 cells to about 800 cells, about 200 cells to about 800 cells, about 300 cells to about 800 cells, or about 400 cells to about 800 cells. In one embodiment, when the three-dimensional cell aggregate has an average diameter of about 150 μm, it may include stem cells of about 400 cells to about 500 cells, and when the three-dimensional cell aggregate has an average diameter of about 200 μm, it may include stem cells of about 600 cells to about 800 cells (e.g., about 700 cells).

The three-dimensional cell culture process may be performed by any three-dimensional cell culture technology known in the art to which the present disclosure pertains. For example, the three-dimensional cell culture process may be a cell culture process using microwell array culture, porous microsphere culture, hanging drop culture, low attachment plate culture, membrane-based cell-detachment culture, thermal lifting culture, centrifugation culture, semi-solid medium culture, etc. (reference: Tissue Engineering: Part B, Volume 20, number 5, 2014). A cell culture vessel or culture support used in the three-dimensional cell culture process may be surface-treated with a biocompatible material such as polyethylene glycol (PEG), etc. The surface-treated culture vessel or culture support is advantageous in uniformly forming size-controlled cell aggregates. In one embodiment, the microwell may be fabricated by a simple well-known microfabrication technique such as soft-lithography.

To allow the cell aggregates produced by the three-dimensional cell culture process to have the average diameter within the above range, a size (average diameter) of a cell culture space (internal space of the vessel or pore) of the culture vessel or culture support such as a microwell or a porous microsphere may be about 50 μm or more, about 70 μm or more, about 100 μm or more, about 130 μm or more, about 150 μm or more, or about 170 μm or more, or about 250 μm, about 230 μm or less, or about 200 μm or less, for example, about 50 μm to about 250 μm, about 50 μm to 230 μm, about 50 μm to about 200 μm, about 70 μm to about 250 μm, about 70 μm to 230 μm, about 70 μm to about 200 μm, about 100 μm to about 250 μm, about 100 μm to 230 μm, about 100 μm to about 200 μm, about 130 μm to about 250 μm, about 130 μm to 230 μm, about 130 μm to about 200 μm, about 150 μm to about 250 μm, about 150 μm to 230 μm, about 150 μm to about 200 μm, about 170 μm to about 250 μm, about 170 μm to 230 μm, or about 170 μm to about 200 μm.

The three-dimensional cell culture process may be performed until the size of the cell aggregates becomes the upper limit by seeding cells in the culture vessel or culture support, for example, in a microwell or each pore of porous microsphere, and culturing the cells using a medium commonly used in the stem cell culture under common conditions (e.g., 37° C., 5% $CO_2$).

For example, in the three-dimensional cell culture using the microwell, the amount of the cells seeded in each microwell may be about 1 cell to about 1000 cells, about 10 cells to about 1000 cells, about 100 cells to about 1000 cells, about 200 cells to about 1000 cells, about 300 cells to about 1000 cells, about 400 cells to about 1000 cells, about 500 cells to about 1000 cells, about 600 cells to about 1000 cells, about 1 cell to about 900 cells, about 10 cells to about 900 cells, about 100 cells to about 900 cells, about 200 cells to about 900 cells, about 300 cells to about 900 cells, about 400 cells to about 900 cells, about 500 cells to about 900 cells, about 600 cells to about 900 cells, about 1 cell to about 800 cells, about 10 cells to about 800 cells, about 100 cells to about 800 cells, about 200 cells to about 800 cells, about 300 cells to about 800 cells, about 400 cells to about 800 cells, about 500 cells to about 800 cells, about 600 cells to about 800 cells, about 1 cell to about 700 cells, about 10 cells to about 700 cells, about 100 cells to about 700 cells, about 200 cells to about 700 cells, about 300 cells to about 700 cells, about 400 cells to about 700 cells, about 500 cells to about 700 cells, or about 600 cells to about 700 cells per microwell, but is not limited thereto. In other methods than the three-dimensional cell culture method using the microwell, the similar cell seeding amount may be also applied, but is not limited thereto. The culture may be performed using an amount which is commonly recognized appropriate for each method.

When the cell aggregates are obtained by the three-dimensional cell culture, cell proliferation does not occur largely, and therefore, the number of seeded cells and the number of cells included in the three-dimensional cell aggregate may be interpreted as being equal.

The cell aggregates obtained by the three-dimensional cell culture may be cultured to induce extracellular vesicles of the cells.

Therefore, in one embodiment, the method of producing the stem cell-derived extracellular vesicles may further include culturing the cell aggregates.

In a specific embodiment, the method of producing the adult stem cell-derived extracellular vesicles may include (1) producing three-dimensional cell aggregates by culturing stem cells by three-dimensional cell culture; and (2) culturing the cell aggregates.

The culturing of the cell aggregates may be performed under common culture conditions (e.g., 37° C., 5% $CO_2$). In this regard, the culturing of the cell aggregates may be performed by shaking culture under stirring, rotating, and/or vibrating to increase production of extracellular vesicles. For example, the shaking culture by stirring, rotating, and/or vibrating may be advantageous in that nutrients and oxygen may be more effectively provided for the three-dimensional cell aggregates.

In one embodiment, the culturing of the cell aggregates may be performed under shaking at a speed of about 40 rpm or less or about 35 rpm or less in consideration of stress applied to the cells. For example, the culturing of the cell aggregates may be performed under shaking at a speed of about 10 rpm to about 35 rpm, about 15 rpm to about 35 rpm, about 20 rpm to about 35 rpm, about 25 rpm to about 35 rpm, or about 30 rpm to about 35 rpm, but is not limited thereto. The shaking culture may be orbital shaking, lateral shaking, circular shaking, etc., and may be performed using a three-dimensional culture apparatus such as an orbital shaker, a rotary wall vessel bioreactor, a spinner flask, etc., but is not limited thereto.

The culturing of the cell aggregates may be performed for 1 day to 30 days, 1 day to 25 days, 1 day to 20 days, 1 day to 17 days, 1 day to 15 days, 1 day to 13 days, 1 day to 10 days, 1 day to 7 days, 1 day to 5 days, 2 days to 30 days, 2 days to 25 days, 2 days to 20 days, 2 days to 17 days, 2 days to 15 days, 2 days to 13 days, 2 days to 10 days, 2 days to 7 days, 2 days to 5 days, 3 days to 30 days, 3 days to 25 days, 3 days to 20 days, 3 days to 17 days, 3 days to 15 days, 3 days to 13 days, 3 days to 10 days, 3 days to 7 days, 3 days to 5 days, 4 days to 30 days, 4 days to 25 days, 4 days to 20 days, 4 days to 17 days, 4 days to 15 days, 4 days to 13 days, 4 days to 10 days, 4 days to 7 days, or 4 days to 5 days.

A culture obtained by culturing the cell aggregates obtained through the three-dimensional cell culture process may include extracellular vesicles secreted from the stem cells. A content of the stem cell-derived extracellular vesicles in the culture of the cell aggregates may be remarkably increased, as compared with a culture obtained by culturing a monolayer culture obtained through a two-dimensional cell culture process. In one embodiment, the content of the stem cell-derived extracellular vesicles in the culture obtained by culturing the cell aggregates obtained through the three-dimensional cell culture process may be about twice or more, about 5 times or more, about 9 times or more, about 10 times or more, about 15 times or more, about 20 times or more, about 25 times or more, about 30 times or more, about 35 times or more, or about 40 times or more, about 45 times or more, about 50 times or more, about 60 times or more, about 70 times or more, about 80 times or more, about 90 times or more, or about 100 times or more, for example, up to about 1000 times, about 700 times, about 500 times, about 200 times, about 150 times, or about 120 times higher than a content of stem cell-derived extracellular vesicles in a culture obtained by culturing a monolayer culture obtained by culturing the same stem cells by a two-dimensional cell culture process (e.g., 2D method described in Example 1; under non-shaking conditions in a general well plate), based on the number of stem cell-derived extracellular vesicles per 100 stem cells, but is not limited thereto.

When the culture obtained by culturing the cell aggregates obtained through the three-dimensional cell culture process is measured using, for example, a fluorescence-activated cell sorting (FACS) method (e.g., measured using a FACSVerse Flow Cytometer (BD bioscience)), the culture may include stem cell-derived extracellular vesicles of about 1 or more, about 2 or more, about 3 or more, about 5 or more, about 10 or more, about 15 or more, about 20 or more, or about 25 or more per 100 cells.

The method of producing the stem cell-derived extracellular vesicles may further include isolating and/or purifying the produced extracellular vesicles after culturing the cell aggregates. The isolating and/or purifying of the extracellular vesicles may be performed by any known common method, for example, centrifuging, filtering, size exclusion column, exoquick, etc., but is not limited thereto.

Another aspect provides a composition for producing the stem cell-derived extracellular vesicles, the composition including the stem cell aggregates. Still another aspect provides a method of producing stem cell-derived extracellular vesicles, the method including culturing the three-dimensional cell aggregates of stem cells. Still another aspect provides use of the cell aggregates of stem cells in producing stem cell-derived extracellular vesicles. The stem cells may be isolated from the living body. The culture may be performed ex vivo.

The culturing of the cell aggregates may be performed by shaking culture, for example, by shaking at a speed of about 10 rpm to about 35 rpm, about 15 rpm to about 35 rpm, about 20 rpm to about 35 rpm, about 25 rpm to about 35 rpm, or about 30 rpm to about 35 rpm, but is not limited thereto.

The stem cells may be adult stem cells, for example, mesenchymal stem cells, more specifically, human mesenchymal stem cells, but are not limited thereto.

The cell aggregates may be a three-dimensional structure produced by three-dimensional cell culture of the stem cells. The three-dimensional cell culture is the same as described above. The cell aggregate may be, for example, a spheroid-shaped structure. The cell aggregate may have an average diameter of about 50 μm or more, about 70 μm or more, about 100 μm or more, about 130 μm or more, about 150 μm or more, or about 170 μm or more, to realize a three-dimensional structure similar to in vivo tissue, and the cell aggregate may have an average diameter of about 250 μm, about 230 μm or less, or about 200 μm or less to prevent necrosis of the cells inside the aggregate due to oxygen depletion. For example, the cell aggregate may have an average diameter of about 50 μm to about 250 μm, about 50 μm to 230 μm, about 50 μm to about 200 μm, about 70 μm to about 250 μm, about 70 μm to 230 μm, about 70 μm to about 200 μm, about 100 μm to about 250 μm, about 100 μm to 230 μm, about 100 μm to about 200 μm, about 130 μm to about 250 μm, about 130 μm to 230 μm, about 130 μm to about 200 μm, about 150 μm to about 250 μm, about 150 μm to 230 μm, about 150 μm to about 200 μm, about 170 μm to about 250 μm, about 170 μm to 230 μm, or about 170 μm to about 200 μm.

Still another aspect provides a culture obtained by culturing the cell aggregates of the stem cells. When the culture of the cell aggregates of the stem cells may be measured using, for example, a fluorescence-activated cell sorting (FACS) method (e.g., measured using a FACSVerse Flow Cytometer (BD bioscience)), it may include stem cell-derived extracellular vesicles of about 1 or more, about 2 or more, about 3 or more, about 5 or more, about 10 or more, about 15 or more, about 20 or more, or about 25 or more, for example, about 1 to about 50, about 2 to about 50, about 3 to about 50, about 5 to about 50, about 10 to about 50, about 15 to about 50, about 20 to about 50, or about 25 to about 50 per 100 cells.

In one embodiment, the number of the stem cell-derived extracellular vesicles included in the culture obtained by culturing the cell aggregates of the stem cells may be about twice or more, about 5 times or more, or about 9 times or more, for example, about twice to about 200 times, about 5 times to about 200 times, about 9 times to about 200 times, about twice to about 150 times, about 5 times to about 1500 times, about 9 times to about 150 times, about twice to about 120 times, about 5 times to about 120 times, about 9 times to about 120 times, about twice to about 100 times, about twice to about 100 times, or about 9 times to about 100 times higher than that of a culture obtained by culturing the same stem cells by the existing common two-dimensional culture method (e.g., 2D method described in Example 1; under non-shaking conditions in a general well plate) (see FIG. 5A to FIG. 9), but is not limited thereto.

The stem cell-derived extracellular vesicle may include various therapeutic factors related with angiogenesis, immuno-modulation, cell migration, anti-apoptosis, etc. For example, the stem cell-derived extracellular vesicle may include various active biomolecules such as proteins (e.g., various growth factors, chemokines, cytokines, transcription factors, etc.), genes, RNAs (various microRNAs, etc.), etc.

Therefore, the culture of the cell aggregates of stem cells including the stem cell-derived extracellular vesicles may be usefully applied to various therapies.

Accordingly, still another aspect provides a pharmaceutical composition including the culture of the cell aggregates of stem cells and/or the extracellular vesicles isolated therefrom. The pharmaceutical composition may be effectively used in the treatment of diseases for which the existing stem cell injection/transplantation therapy has been applied, such as central nervous system diseases (e.g., stroke, dementia, spinal cord injury, Parkinson's disease, etc.), arthritis, kidney disease, cancer, etc.

The pharmaceutical composition may be administered to a subject via various administration routes, such as oral administration or parenteral administration. For example, the pharmaceutical composition may be injected or transplanted into a lesion site of a subject, or administered via a parenteral route such as intravascular administration (intravenous or intraarterial administration), subcutaneous administration, etc., but is not limited thereto.

The subject to which the pharmaceutical composition is administered may be an animal selected from mammals including primates such as humans, monkeys, etc., rodents such as rats, mice, etc., ayes, etc., and/or a (isolated) tissue or cell derived therefrom, or a culture thereof.

The stem cells, from which the culture of the cell aggregate of stem cells included as an active ingredient in the pharmaceutical composition is obtained, may be homologous stem cells derived from the same species as the subject, autologous stem cells derived from the subject's own body, or a mixture thereof.

Advantageous Effects of Disclosure

Recently, adult stem cell injection/transplantation therapies have been actively applied in the treatment of various incurable/intractable diseases (stroke, arthritis, dementia, various kidney diseases, various neurological diseases, cancer, etc.), and the present disclosure may be applied as an alternative therapy to alleviate risk factors that are generated from a therapy of transplanting/injecting living stem cells.

BRIEF DESCRIPTION OF DRAWINGS

FIG. 2 shows photographs showing results of observation of cultures which were cultured for 3 days by a three-dimensional cell culture process and a two-dimensional cell culture process under a microscope;

FIG. 10 shows images showing a cytokine array of therapeutic factors included in stem cell-derived extracellular vesicles.

BEST MODE

Hereinafter, the present disclosure will be described in more detail with reference to Examples. However, these Examples are for illustrative purposes only, and the scope of the present disclosure is not intended to be limited by these Examples.

Example 1: Three-Dimensional Cell Culture of Mesenchymal Stem Cells

Figure 1:
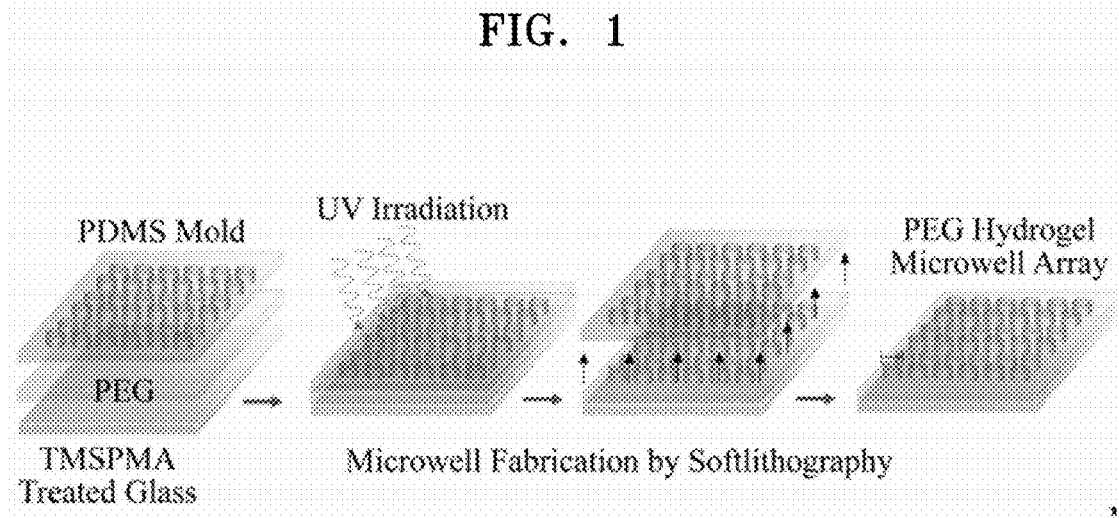
FIG. 1 illustrates a process of fabricating a polyethylene glycol (PEG) hydrogel microwell array using a soft lithography microfabrication technique.

For three-dimensional cell culture of mesenchymal stem cells, a polyethylene glycol (PEG) hydrogel microwell array fabricated using a soft lithography microfabrication technique was prepared (including 1225 200 μm-sized microwells per array) (see FIG. 1). Human bone marrow-derived mesenchymal stem cells cultured in a laboratory were seeded on the PEG microwell array (600-700 cells/microwell). The mesenchymal stem cells spontaneously aggregated in the microwells to form cellular aggregates with a uniform size within 12 hours (a spheroidal structure having an average diameter of about 200 μm). As a result, 1225 mesenchymal stem cell aggregates having the spheroidal structure (an average diameter of about 200 μm) per array were cultured. A large amount of mesenchymal stem cell spheroids with a uniform size was produced from a number of microwell arrays, and then the mesenchymal stem cell spheroids in the microwell array were cultured under orbital shaking at a speed of about 35 rpm (culture conditions: 37° C.; 5% $CO_2$, a total culture period: 3 days, 5 days, or 7 days; medium: low glucose DMEM (Invitrogen)+10% FBS+1% antibiotics).

The three-dimensional mesenchymal stem cell spheroidal structures having a uniform size obtained by the culturing were cultured under shaking at a speed of 35 rpm in an orbital shaker (Multi shaker 3D-200, FINE PCR, Korea) for total 3 days, 5 days, or 7 days including the spheroid production time.

For comparison, two-dimensional culture (2D & 2D with shaking) was performed. In detail, a two-dimensional culture group (2D) was cultured in a general 6-well plate without shaking for total 3 days, 5 days, or 7 days as in the above method, and a two-dimensional culture group with shaking (2D with shaking) was cultured under shaking at a speed of 35 rpm for total 3 days, 5 days, or 7 days as in the above method.

Morphologies of the obtained mesenchymal stem cell cultures were observed and shown in FIG. 2. In FIG. 2, the top image is a microscopic image of a two-dimensional culture group having a cell density of $1 \times 10^5$ cells/cm$^2$ (hMSCs on 2D). The middle image is a microscopic image of 1225 spheroids at 12 hours after seeding $5 \times 10^5$ 2D-cultured mesenchymal stem cells in a microwell array having 1225 microwells (DO MSC spheroid in microwells). The bottom image is an image obtained after transferring the produced 1225 spheroids to a bacterial grade (cell non-adhesive) petri-dish and culturing them under shaking at 35 rpm for 3 days (D3 MSC spheroid in suspension with shaking (35 rpm)). As shown in FIG. 2, it was confirmed that one mesenchymal stem cell spheroid with a uniform size was formed in each microwell by the three-dimensional cell culture, unlike two-dimensional cell culture.

Figure 3:
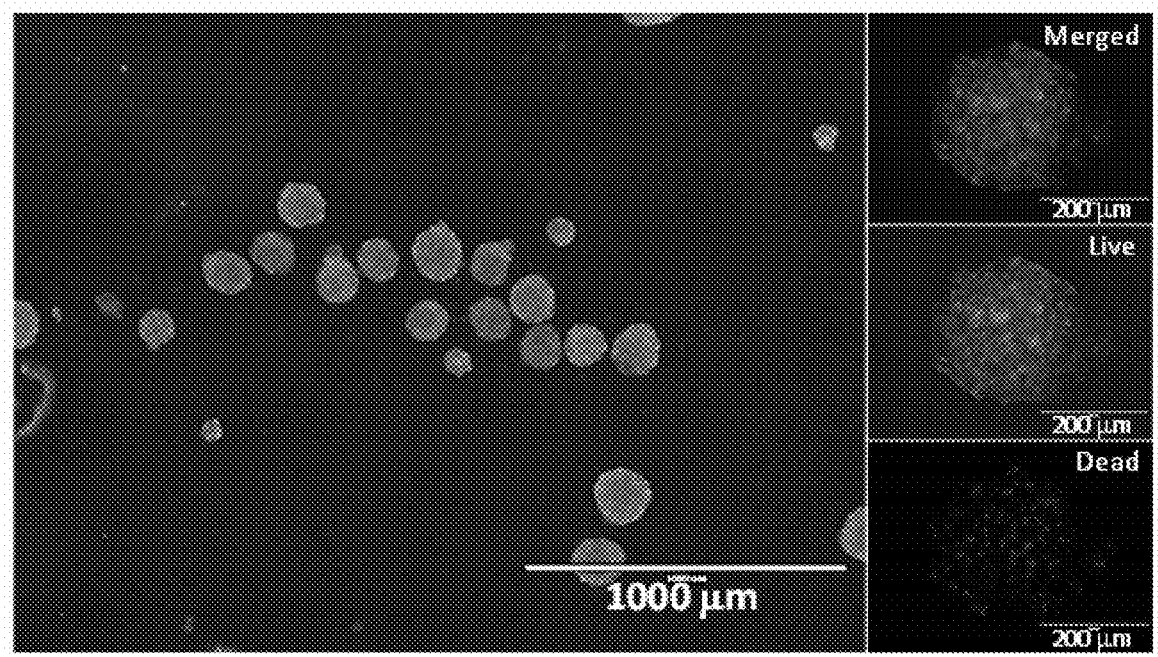
FIG. 3 shows photographs showing results of a live and dead assay of a culture which was cultured for 3 days by the three-dimensional cell culture process.

To examine activities of the cultured cells, the culture obtained by the three-dimensional cell culture (3 day-shaking culture) was subjected to a Live & Dead assay using a live and dead assay kit (Invitrogen) in accordance with the manufacturer's manual. The obtained results are shown in FIG. 3. As shown in FIG. 3, it was confirmed that most cells inside the mesenchymal stem cell spheroids were alive.

Example 2: Quantification of Extracellular Vesicles

The liquid cultures obtained by the three-dimensional cell culture (with shaking culture for total 3 days, 5 days, or 7 days) in Example 1 were recovered. The recovered liquid cultures were centrifuged at 2,500 g once and at 14,000 g twice to obtain extracellular vesicles secreted from stem cells in the liquid culture, and then the amounts of mesenchymal stem cell-derived extracellular vesicles in the liquid cultures were analyzed by a fluorescence-activated cell sorting (FACS) method using an anti-CD105 antibody (Becton Dickinson, MCA1557F) specific to cell membrane of human mesenchymal stem cells and an anti-annexin V antibody (Becton Dickinson, 550474) specific to phospholipid membrane. For comparison, with respect to the two-dimensional culture group (2D) and the two-dimensional culture group with shaking (2D with shaking) described in Example 1, the amounts of mesenchymal stem cell-derived extracellular vesicles in the liquid cultures were also quantified in the same manner as above.

In detail, the FACS method was carried out as follows: 20 μl of the obtained extracellular vesicles were suspended in the equal volume of sterile PBS. Each 5 μl of APC fluorescence-conjugated annexin V (lipid membrane marker) and FITC fluorescence-conjugated CD105 (human MSC marker) positive markers (respective antibodies for annexin V and CD105) was added. This procedure demonstrated that microvesicles measured in the present Example were derived from human MSCs. 10 μl of counting beads was added thereto, followed by vortexing. 5 μl of $10 \times Ca^{2+}$ binding buffer (Sigma) was added thereto to allow binding of annexin V and CD105. 5 μl of PBS was added for dilution, and then 400 μl of $10 \times Ca^{2+}$ binding buffer was added for dilution. The prepared samples were measured using a FACSVerse Flow Cytometer (BD bioscience).

With respect to the obtained measured values, BD FACSuite software (BD bioscience) was used to determine a pure extracellular vesicle area. Total extracellular vesicles, Annexin V and CD105 marker-positive extracellular vesicles, and counting beads included in the area were measured for 180 seconds.

Figure 4A:
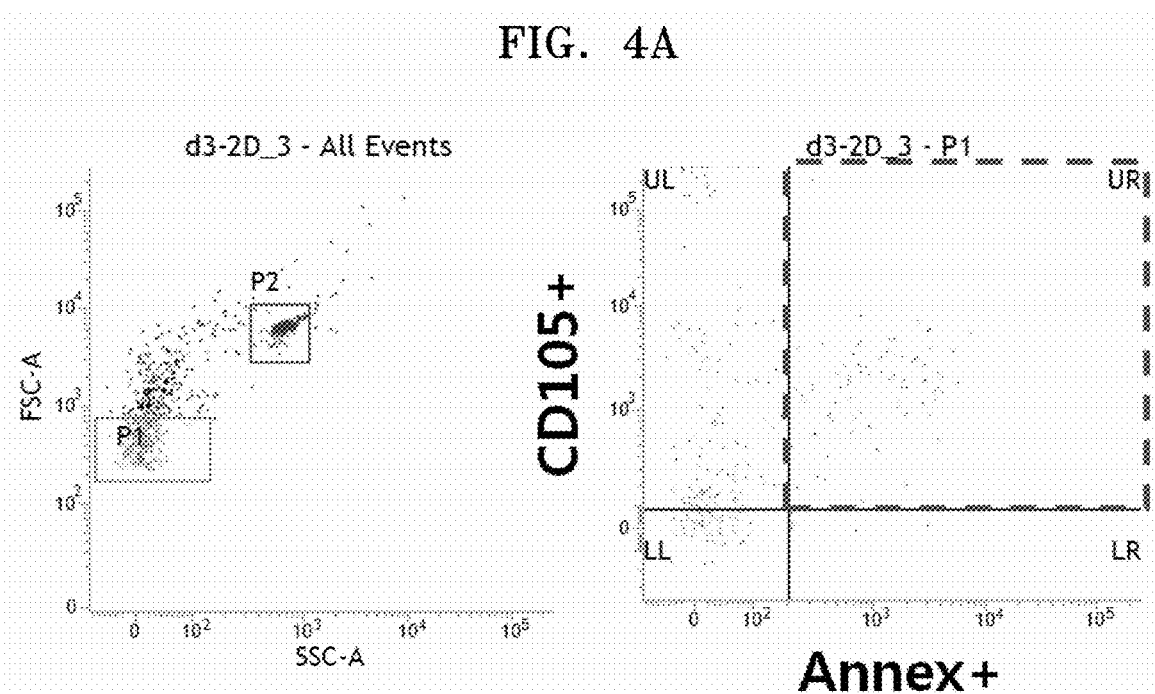
FIGS. 4A to 4D are FACS graphs for extracellular vesicles which were obtained by two-dimensional culture (2D), two-dimensional culture with shaking (2D w/shaking), three-dimensional culture (3D), and three-dimensional culture with shaking (3D w/shaking) for 3 days (4A: 3-day & 2D culture, 4B: 3-day & 2D w/shaking culture, 4C: 3-day & 3D culture, and 4D: 3-day & 3D w/shaking culture)
Figure 4B:
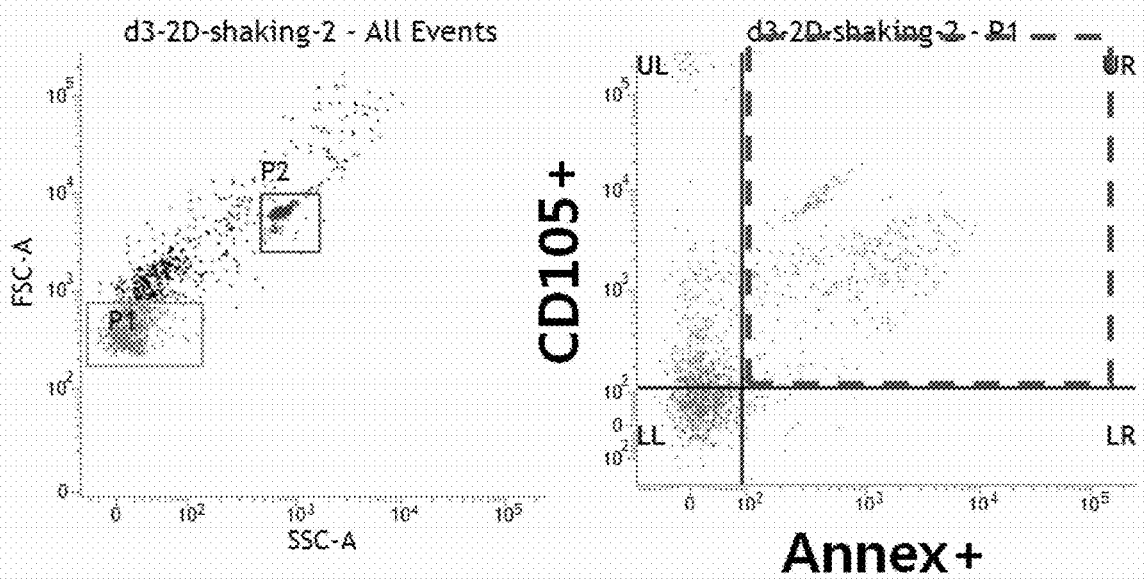
Figure 4C:
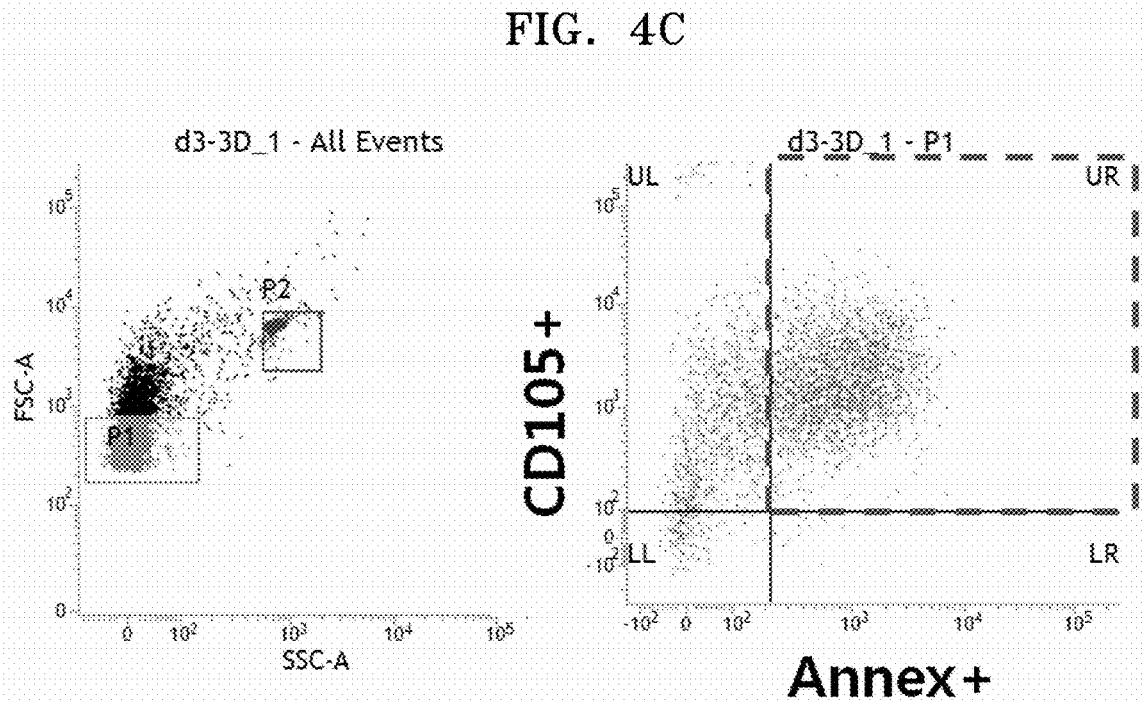
Figure 4D:
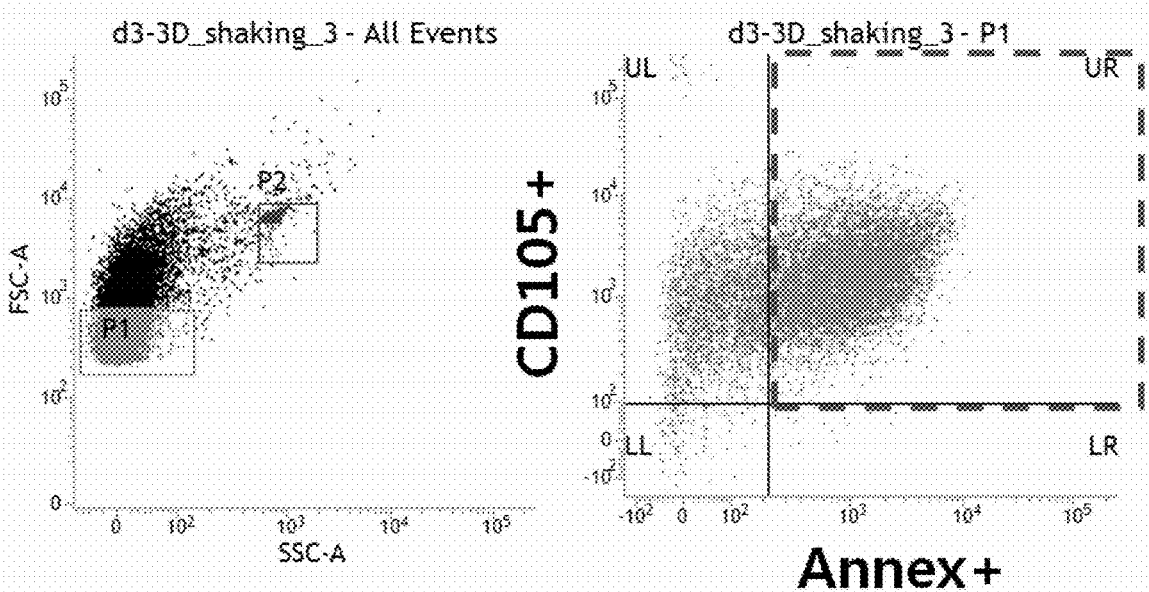
Figure 5A:
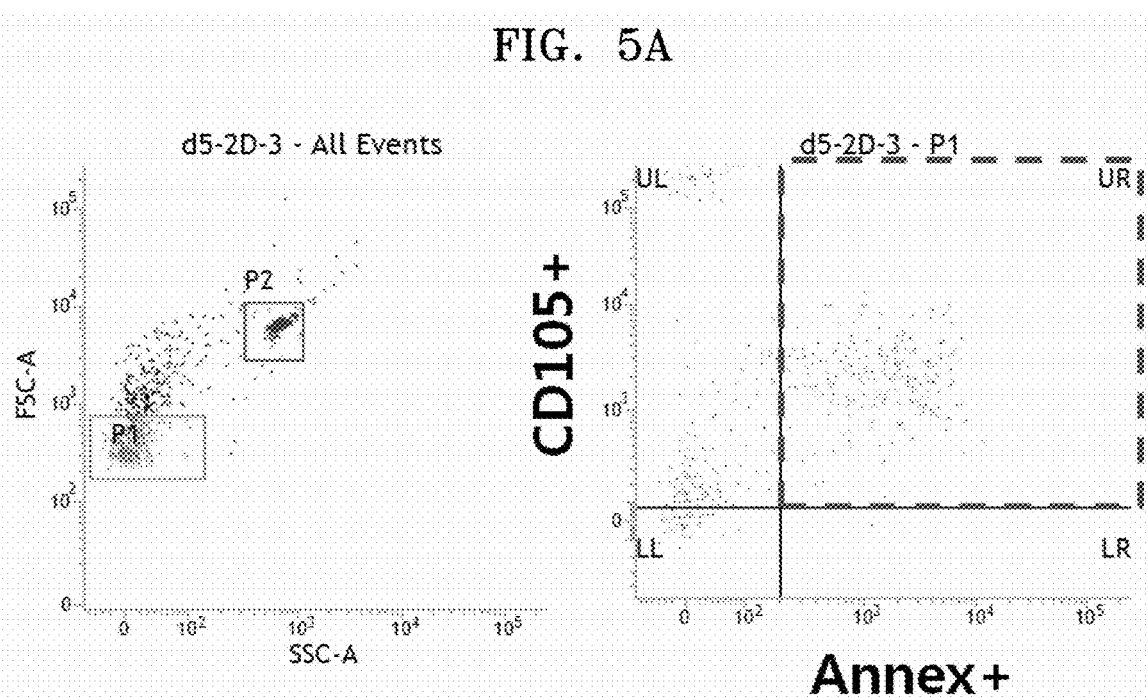
FIGS. 5A to 5D are FACS graphs for extracellular vesicles which were obtained by two-dimensional culture (2D), two-dimensional culture with shaking (2D w/shaking), three-dimensional culture (3D), and three-dimensional culture with shaking (3D w/shaking) for 5 days (5A: 5-day & 2D culture, 5B: 5-day & 2D w/shaking culture, 5C: 5-day & 3D culture, and 5D: 5-day & 3D w/shaking culture)
Figure 5B:
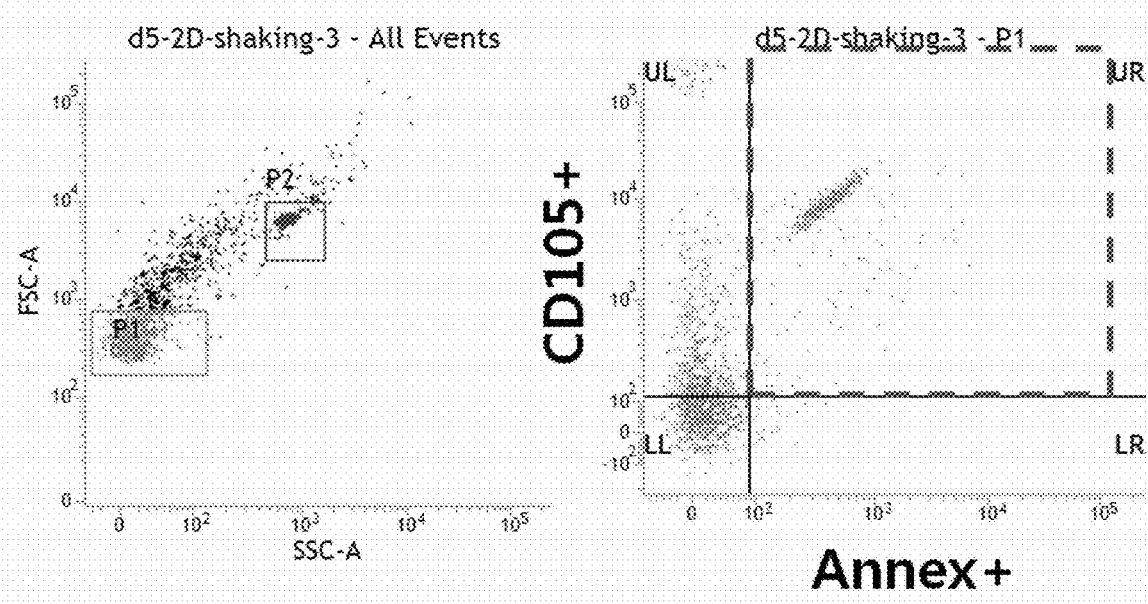
Figure 5C:
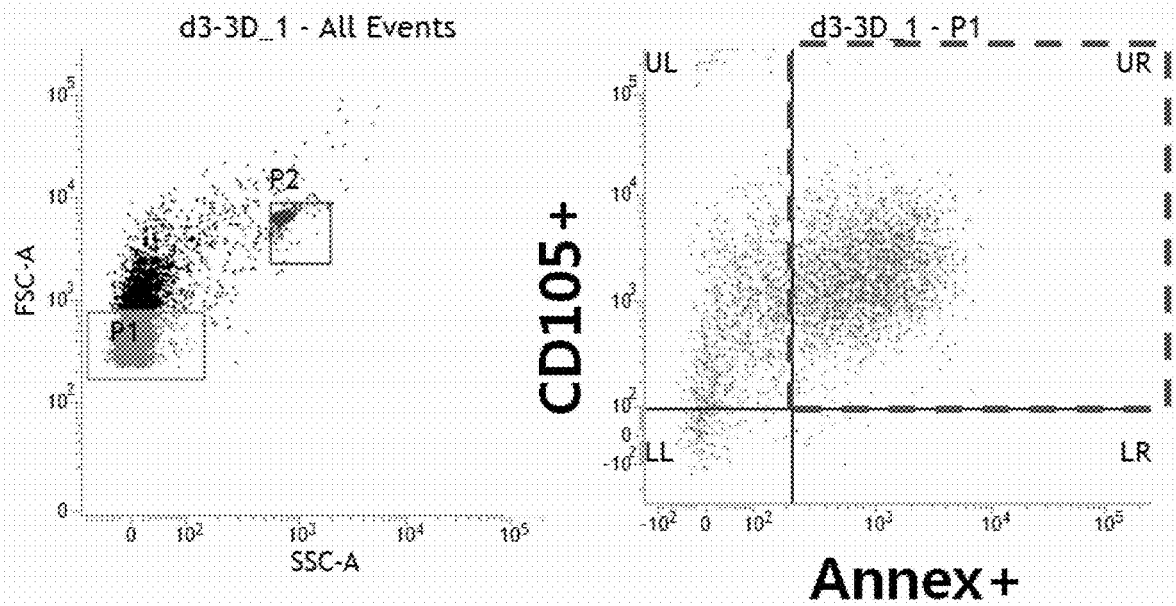
Figure 5D:
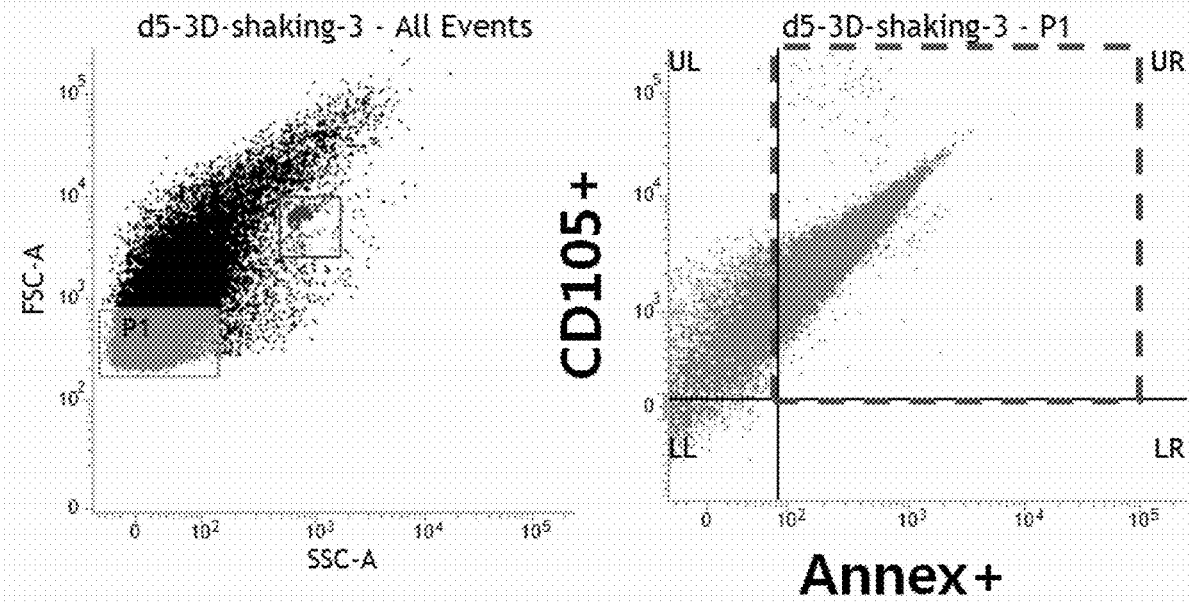
Figure 6A:
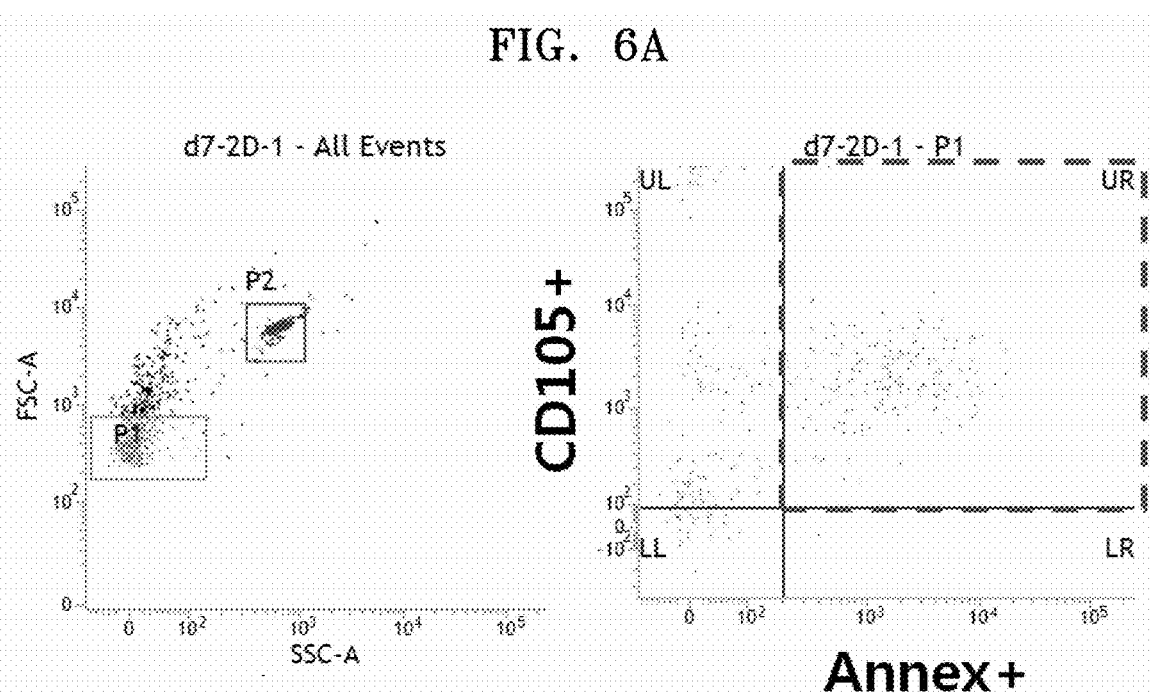
FIGS. 6A to 6D are FACS graphs for extracellular vesicles which were obtained by two-dimensional culture (2D), two-dimensional culture with shaking (2D w/shaking), three-dimensional culture (3D), and three-dimensional culture with shaking (3D w/shaking) for 7 days (6A: 7-day & 2D culture, 6B: 7-day & 2D w/shaking culture, 6C: 7-day & 3D culture, and 6D: 7-day & 3D w/shaking culture)
Figure 6B:
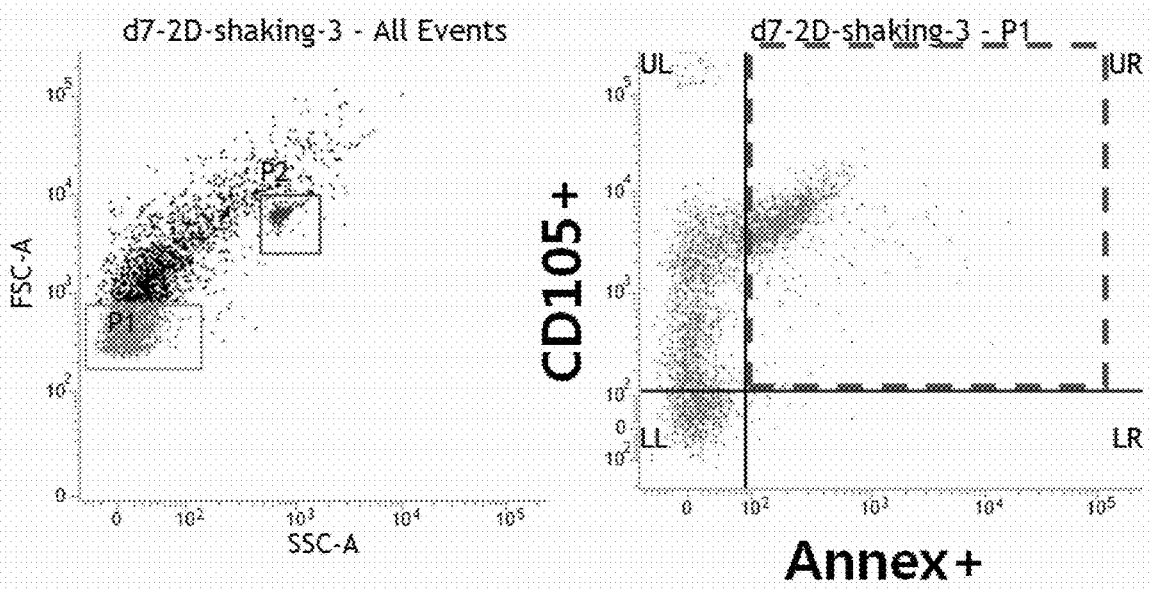
Figure 6C:
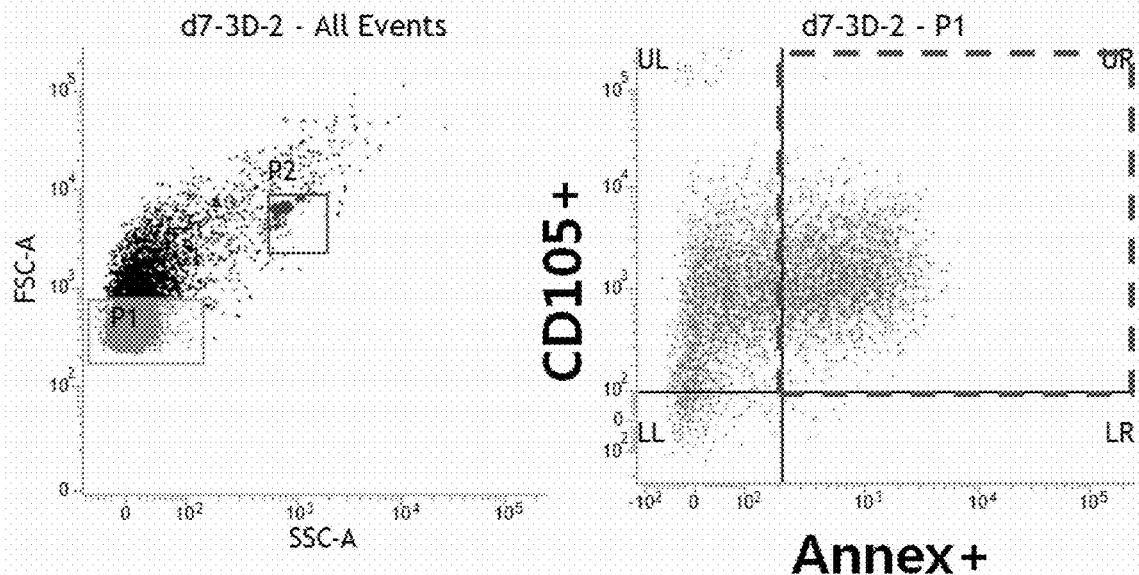
Figure 6D:
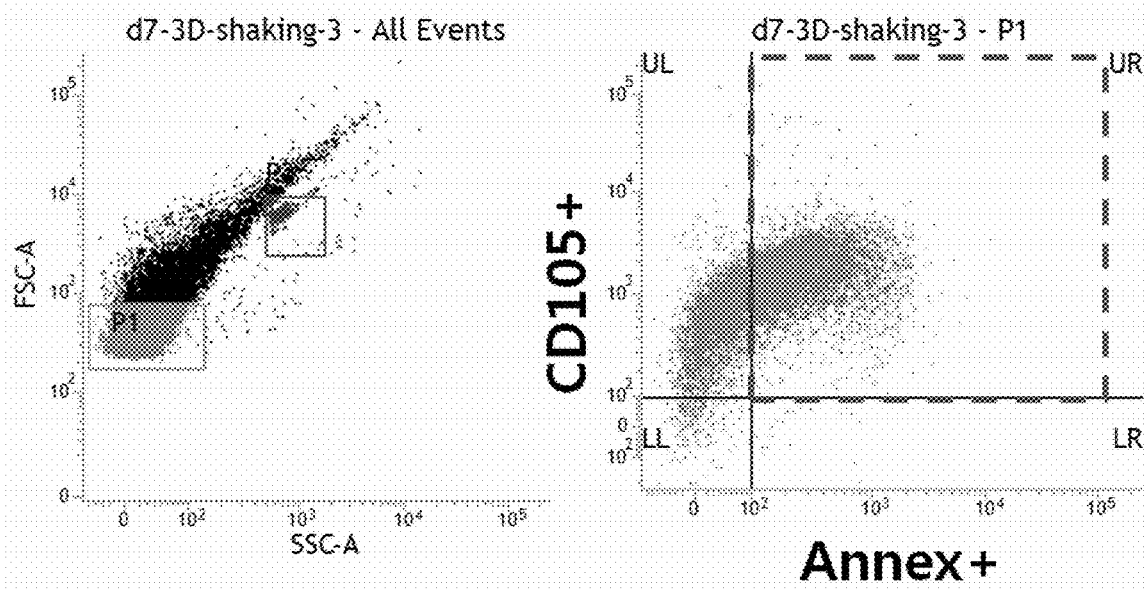

The obtained results are shown in FIG. 4A (3 days & 2D culture), FIG. 4B (3 days & 2D w/shaking culture), FIG. 4C (3 days & 3D culture), FIG. 4D (3 days & 3D w/shaking culture), FIG. 5A (5 days & 2D culture), FIG. 5B (5 days & 2D w/shaking culture), FIG. 5C (5 days & 3D culture), FIG. 5D (5 days & 3D w/shaking culture), FIG. 6A (7 days & 2D culture), FIG. 6B (7 days & 2D w/shaking culture), FIG. 6C (7 days & 3D culture), and FIG. 6D (7 days & 3D w/shaking culture), respectively. In the left graph of each figure, P1 represents restriction of the particle size within 1 μm, and P2 represents FACS counting of microbeads with the known size for reliability of the size restriction of P1. A ratio of the value counted in P2 to the number of microbeads actually added is reliability of the number of vesicles counted in P1. Dots on the right graph are the dots of the area selected by the red box in P1, and the dots in the blue box are vesicles positive for both annexin V and CD105, and the number was used as quantification data of vesicles.

Figure 7:
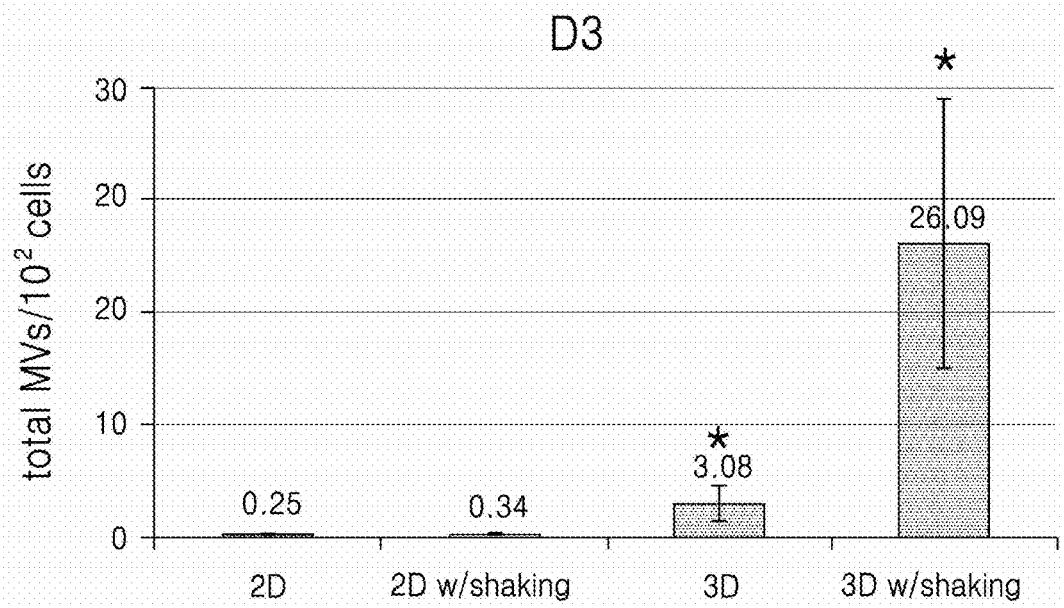
FIG. 7 is a graph showing the number of extracellular vesicles which were obtained by two-dimensional culture (2D), two-dimensional culture with shaking (2D w/shaking), three-dimensional culture (3D), and three-dimensional culture with shaking (3D w/shaking) for 3 days.
Figure 8:
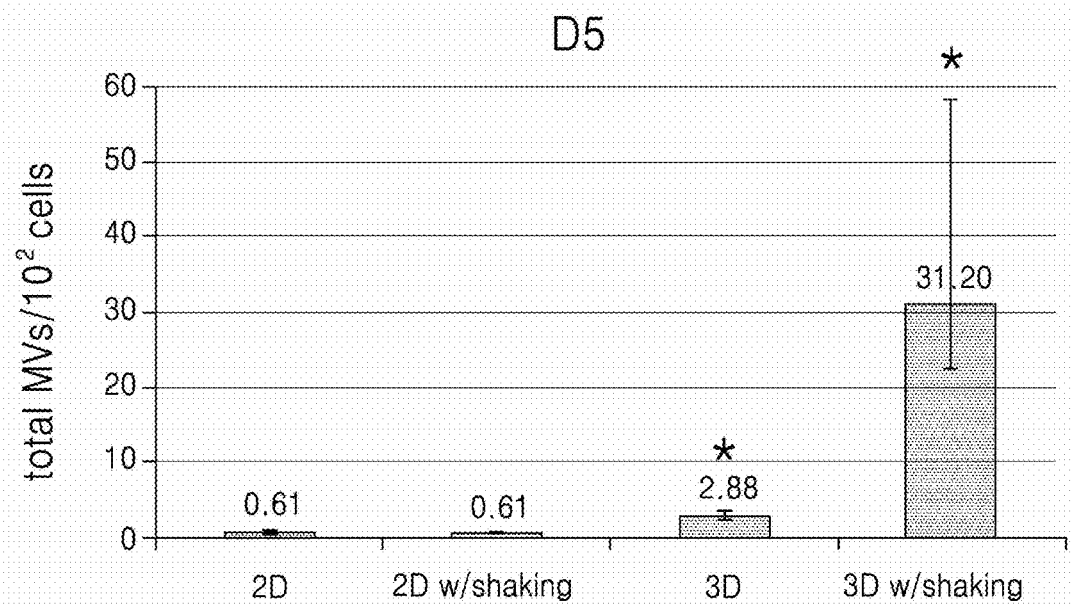
FIG. 8 is a graph showing the number of extracellular vesicles which were obtained by two-dimensional culture (2D), two-dimensional culture with shaking (2D w/shaking), three-dimensional culture (3D), and three-dimensional culture with shaking (3D w/shaking) for 5 days.
Figure 9:
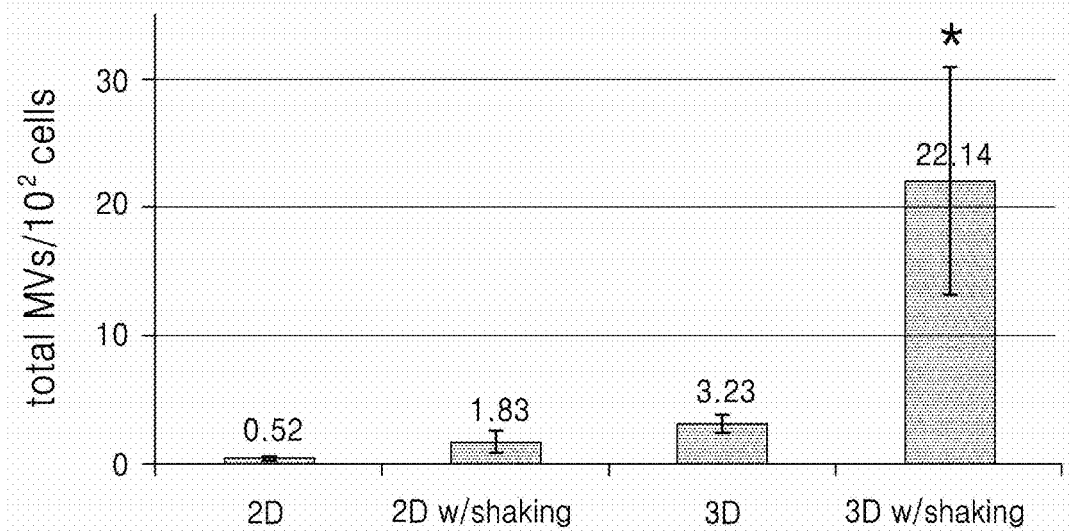
FIG. 9 is a graph showing the number of extracellular vesicles which were obtained by two-dimensional culture (2D), two-dimensional culture with shaking (2D w/shaking), three-dimensional culture (3D), and three-dimensional culture with shaking (3D w/shaking) for 7 days.

The number of extracellular vesicles positive for annexin V and CD105 markers, represented by the blue dotted box in the right graph of FIGS. 4A to 6D, was measured, respectively and then normalized to obtain a graph, which was shown in FIG. 7 (3 day-culture; corresponding to FIGS. 4A to 4D), FIG. 8 (5 day-culture; corresponding to FIGS. 5A to 5D), and FIG. 9 (7 day-culture; corresponding to FIGS. 6A to 6D), respectively.

As shown in FIGS. 5A to 9, the number (Total MVs) of extracellular vesicles positive for Annexin V and CD105, representing that those are derived from human mesenchymal stem cells, was increased about 9 times to about 12 times by the three-dimensional culture (3D) and about 77 times to about 100 times by the three-dimensional culture with shaking (3D w/shaking) for 3 days (D3), as compared with the two-dimensional culture (2D or 2D w/shaking); about 5 times by the three-dimensional culture (3D) and about 51 times by the three-dimensional culture with shaking (3D w/shaking) for 5 days (D5), as compared with the two-dimensional culture (2D or 2D w/shaking); about twice to about 6 times by the three-dimensional culture (3D) and about 12 times to about 43 times by the three-dimensional culture with shaking (3D w/shaking) for 7 days (D7), as compared with the two-dimensional culture (2D or 2D w/shaking). These results suggest that human mesenchymal stem cell-derived extracellular vesicles are remarkably increased by the three-dimensional culture (with or without shaking), as compared with the two-dimensional culture.

Example 3: Analysis of Therapeutic Factors Included in Mesenchymal Stem Cell-Derived Extracellular Vesicles Produced by Three-Dimensional Cell Culture Therapeutic factors included in the mesenchymal stem cell-derived extracellular vesicles produced by the three-dimensional cell culture were analyzed by a cytokine array method, and all the following procedures were performed using a Proteome Profiler™ Human XL Cytokine Array Kit purchased from R&D systems and components included in the kit (buffers, membranes, antibodies, etc.) in accordance with the manufacturer's manual.

Proteins of the extracellular vesicles secreted from the mesenchymal stem cell spheroids obtained in Example 2 (obtained by 3D w/shaking culture) were dissolved using a lysis buffer. A membrane coated with different antibodies was placed in a tray, and blocked with a blocking buffer. After blocking, 200 μg of each sample was added thereto, and allowed to react at 4° C. overnight. The membrane was washed with 1× wash buffer three times and reacted with a detection antibody, and then washed with 1× wash buffer three times. Streptavidin-HRP was added thereto, and allowed to react, and then the membrane was washed with 1× wash buffer three times. The membrane was exposed to x-ray film in a dark room for 10 minutes.

For comparison, the same stem cells as in Example 1 (human bone marrow-derived mesenchymal stem cells) were cultured by two-dimensional culture (see 2D culture of Example 1; 3 day-culture), and treated with an ischemic brain extract (IBE) for 24 hours. The obtained culture was subjected to the same experiment as above. It is known that IBE treatment of stem cells cultured by two-dimensional culture may induce secretion of vesicles including many therapeutic factors. In the present experiment, this two-dimensional culture was used as a positive control group including therapeutic factors.

Preparation and treatment of IBE were carried out as follows: the brain of an animal model with transient middle cerebral artery occlusion (rat; prepared with reference to "Kutluay Uluc, et al.; Focal Cerebral Ischemia Model by Endovascular Suture Occlusion of the Middle Cerebral Artery in the Rat; Journal of Visualized Experiments (2011)") was collected, and 150 mg/ml thereof was aliquoted in Knock-out DMEM (Invitrogen), and then homogenized using a homogenizer. The homogenized brain was collected and centrifuged at 10,000 g for 10 minutes. A supernatant was transferred to a tube, and filtered using a 0.2 μm syringe filter. After filtering, 1 ml thereof was aliquoted and centrifuged at 10° C. and 14,000 g for 45 minutes. Each supernatant was collected in a tube. 20% IBE-medium (16 ml of knock out media+4 ml of IBE) was prepared using a knock out media, and the prepared IBE-medium was filtered using a bottle top filter (0.2 μm) to eliminate contaminants and residual microparticles. The medium cultured for 3 days in 2D mesenchymal stem cell culture dish was removed, followed by PBS washing three times and treatment with 20% (v/v) IBE. After 24 hours, the medium was collected to obtain extracellular vesicles, which were analyzed in the same manner as above.

Figure 11:
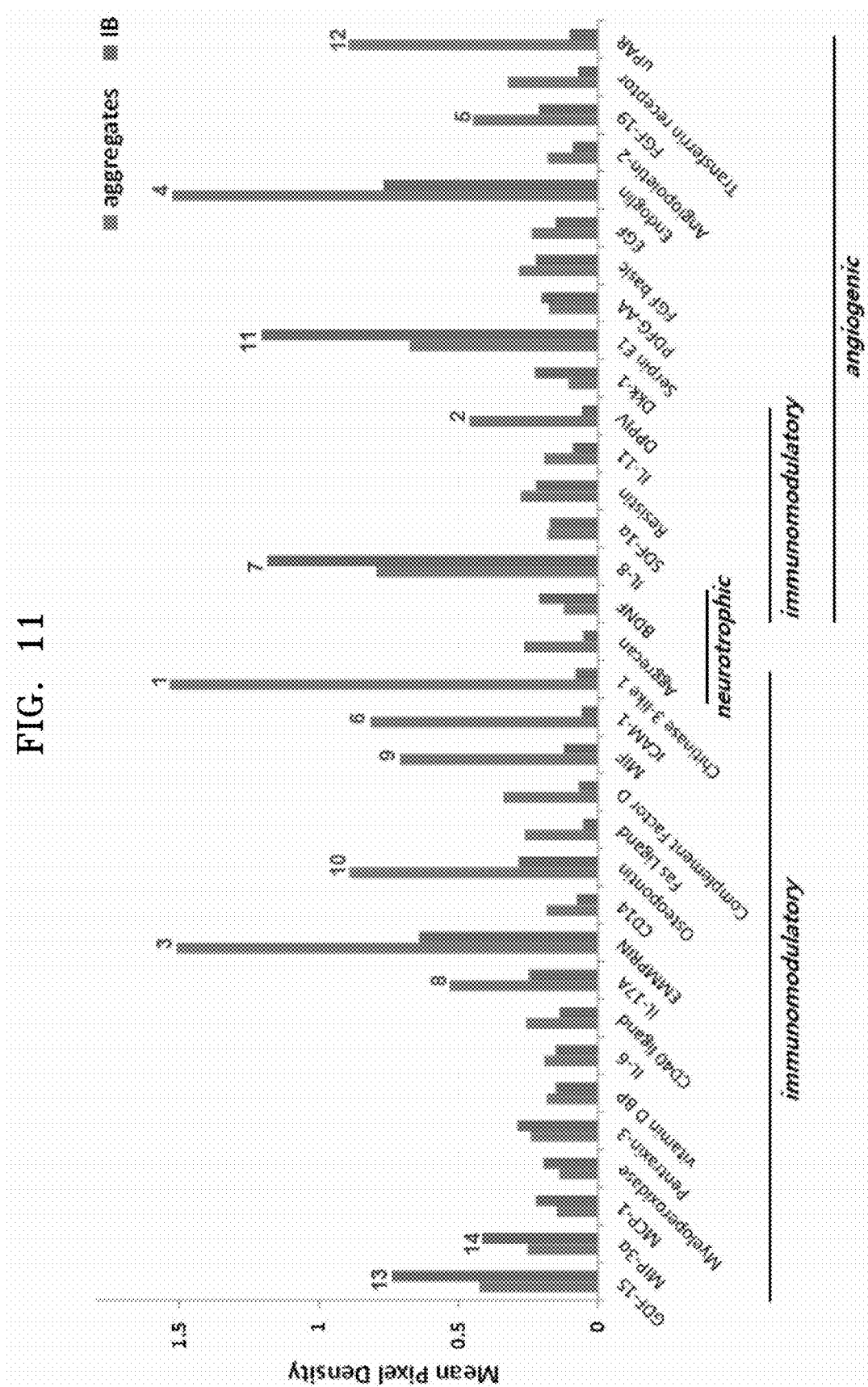
FIG. 11 is a graph showing quantification results of the image of FIG. 10 (left bar (blue): aggregates; right bar (red); IBE).

The developed images are shown in FIG. 10, and quantification results thereof are shown in FIG. 11. As shown in FIGS. 10 and 11, the extracellular vesicles secreted from the mesenchymal stem cell spheroids (represented by hMSC-aggregates or aggregates) were confirmed to include a large amount of various kinds of therapeutic factors, equal to or higher than those of IBE treatment.

The invention claimed is:

1. A method of mass-producing stem cell-derived extracellular vesicles, the method comprising:
  (a) spontaneously producing three-dimensional cell aggregates by culturing human bone marrow-derived mesenchymal stem cells by a three-dimensional cell culture process, wherein the three-dimensional cell culture process does not comprise a centrifugation culture;
  (b) culturing the produced three-dimensional cell aggregates by a shake culture process for 3 to 10 days; and
  (c) obtaining extracellular vesicles from a culture of the cell aggregates;
  wherein the extracellular vesicles obtained in (c) comprise more immunomodulatory factors, neurotrophic factors or angiogenic factors than extracellular vesicles obtained from a two-dimensional stem cell culture treated with ischemic brain extract, and
  wherein the immunomodulatory factors are selected from the group consisting of Complement Factor D, IL-6, IL-11, IL-17A, EMMPRIN, Osteopontin, DPP IV, Fas Ligand, MIF and ICAM-1, the neurotrophic factors are selected from the group consisting of Chitinase 3 like1 and Aggrecan, and the angiogenic factors are selected from the group consisting of DPP IV, EGF, Endoglin, Resistin, Angiopoietin 2, FGF-19 and uPAR.

2. The method of claim 1, wherein the extracellular vesicles have an average diameter of 50 nm to 1 μm.

3. The method of claim 1, wherein a size of a cell culture space of a culture vessel or a culture support used in the three-dimensional cell culture process is 50 μm to 250 μm.

4. The method of claim 3, wherein the size of the cell culture space of the culture vessel or the culture support used in the three-dimensional cell culture process is 100 μm to 200 μm.

5. The method of claim 1, wherein the cell aggregates have an average diameter of 50 μm to 250 μm.

6. The method of claim 5, wherein the cell aggregates have an average diameter of 100 μm to 200 μm.

7. The method of claim 1, wherein the cell aggregates are cultured by a shake culture process for 3 to 7 days.

8. The method of claim 1, wherein the cell aggregates are cultured by a shake culture process for 3 days.

* * * * *